US00PP15721P2

(12) United States Plant Patent
Heims

(10) Patent No.: US PP15,721 P2
(45) Date of Patent: Apr. 12, 2005

(54) ***ATHYRIUM* PLANT NAMED 'PEWTER LACE'**

(50) Latin Name: ***Athyrium niponicum* var. *pictum***
Varietal Denomination: Pewter Lace

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 14 days.

(21) Appl. No.: 10/872,350

(22) Filed: Jun. 18, 2004

(51) Int. Cl.[7] ..... A01H 9/00
(52) U.S. Cl. ..... Plt./379
(58) Field of Search ..... Plt./379

(56) References Cited

U.S. PATENT DOCUMENTS

PP12,803 P2 * 7/2002 Ballantyne ..... Plt./379
PP15,072 P2 * 8/2004 Heims ..... Plt./379

* cited by examiner

*Primary Examiner*—Kent Bell
*Assistant Examiner*—W C Haas
(74) *Attorney, Agent, or Firm*—Klarquist Sparkman LLP

(57) ABSTRACT

A new and distinct cultivar of *Athyrium niponicum* var. *pictum* plant characterized by the pewter tone to the leaves, silver over grey green, with a pink rachis. This coloring persists from new growth to mature.

1 Drawing Sheet

Botanical classification: *Athyrium niponicum* var. *pictum.*
Variety denomination: 'Pewter Lace'.

The present invention relates to a new and distinct cultivar of *Athyrium niponicum* var. *pictum,* of the family Woodsiaceae, which originated as a chance sporling found by Dan Heims.

The new variety has been reproduced only by asexual propagation (division and tissue culture). Each of the clones exhibits identical characteristics to the original selection.

This plant is characterized by the pewter tone to the leaves, silver over grey green, with a pink rachis. This coloring persists from new growth to mature.

Asexual propagation by division and tissue culture as done in Canby, Oreg., shows that the foregoing characteristics and distinctions come true to type and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a three-year-old *Athyrium niponicum* var. *pictum* 'Pewter Lace' in a container in Canby, Oreg.

DETAILED PLANT DESCRIPTION

The following is a detailed description of the new *Athyrium niponicum* var. *pictum* selection based on observations of 2½ year old specimens grown in a 3-gallon container in a cool greenhouse in Canby, Oreg. The color descriptions are all based on The Royal Horticultural Society Colour Chart.

Botanical name: *Athyrium niponicum* var. *pictum.*
Variety denomination: 'Pewter Lace'.
Plant:
- *Form.*—Terrestrial, rhizomatous fern.
- *Hardiness.*—U.S.D.A. Zones 5 to 8.
- *Size.*—62 cm wide and 40 cm tall.

Stem: None above ground, rhizomatous. Rhizome is typical of *Athyrium nipponicum*

Foliage:
- *Type.*—Compound.
- *Shape.*—Lanceolate. Twice pinnate. Pinnule is lanceolate to oblong.
- *Size.*—Grows to 50 cm long and 26 cm wide. Pinnules may be from 3 to 17 cm long and from 1 to 3 cm wide.
- *Margins.*—2-pinnate. Pinnule is lobed and incised.
- *Apex.*—Acuminate, pinnatifid.
- *Base.*—Rounded to truncate.
- *Texture.*—Dry, papery.
- *Petiole texture.*—Glabrous but with chaffy scales (Greyed Orange 172A), mainly along the base but occasional elsewhere.
- *Petiole length.*—15 cm.
- *Petiole color.*—Between Greyed Purple 187A and Brown 200A. Old leaves are Yellow Green 146A with a burgundy line down the center (same color as younger leaves).
- *Leaf color.*—Topside: Overall look is a purplish gray green (Closest to Yellow Green 147A with burgundy tones) with a white overlay (between White 155B and Greyed Green 196D) everywhere except near rachis. The main vein of the pinnae is burgundy, Greyed Purple 187A, bleeding to light burgundy (Greyed Purple 187D) on each pinnae where there is a white overlay. Bottom side: Closest to Yellow Green 147A. New spring leaves: Closest to Brown 200A.

Fruiting body: Same as all *Athyrium niponicum* var. *pictum.*
- *Type.*—Sporangium.
- *Fertility.*—Fertile.
- *Sori.*—Shape — Covered with a superior confluent indusium, elongate, opening on one edge, the edge facing the end of the pinnae. Location — Dorsal, on every pinnule, mostly on one side of the vein. Where on both sides it curls around to the other side near the tip. Size — Varies with the pinnule size, usually 1 to 2 mm. long. Immature — Brown Group 200D. Sporulating — Brown 200B.

Diseases and pests: Some *Athyrium* are prone to rust. No diseases have been observed on plants grown commercially in Canby, Oreg. *Athyrium* generally have no pest problems.

COMPARISONS

The instant plant resulted from a selection of *Athyrium niponicum* var. *pictum. A. niponicum,* as described in *A–Z Encyclopedia of Garden Plants* by the American Horticultural Society (1996), is a "Deciduous fern with creeping red-brown rhizomes and 2- or 3-pinnate to pinnatifid, lance-shaped, silvery gray-green or mid-green fronds, to 14 in (35 cm) long, with red-purple midribs. . . . Segments are lance-shaped to oblong or ovate, sometimes with notched or lobed margins . . . [var. *pictum*] has fronds with purplish red stalks and silver-gray segments, sometimes flushed purple-red."

The instant plant differs from *A. niponicum* var. *pictum* 'Ursula's Red' (unpatented), in the background color of the leaf being a deeper yellow green color (Yellow Green 147A rather than 146A).

Compared to *A. niponicum* var. *pictum* 'Silver Falls' (U.S. Plant Pat. No. 12,803), the instant plant has a deeper yellow green color to the leaves and more pink coloration in the rachis and pinnae.

I claim:

1. A new and distinct *Athyrium niponicum* var. *pictum* plant substantially as shown and described, characterized by the pewter tone to the leaves, silver over grey green, with a pink rachis, said coloring persisting from new to mature growth.

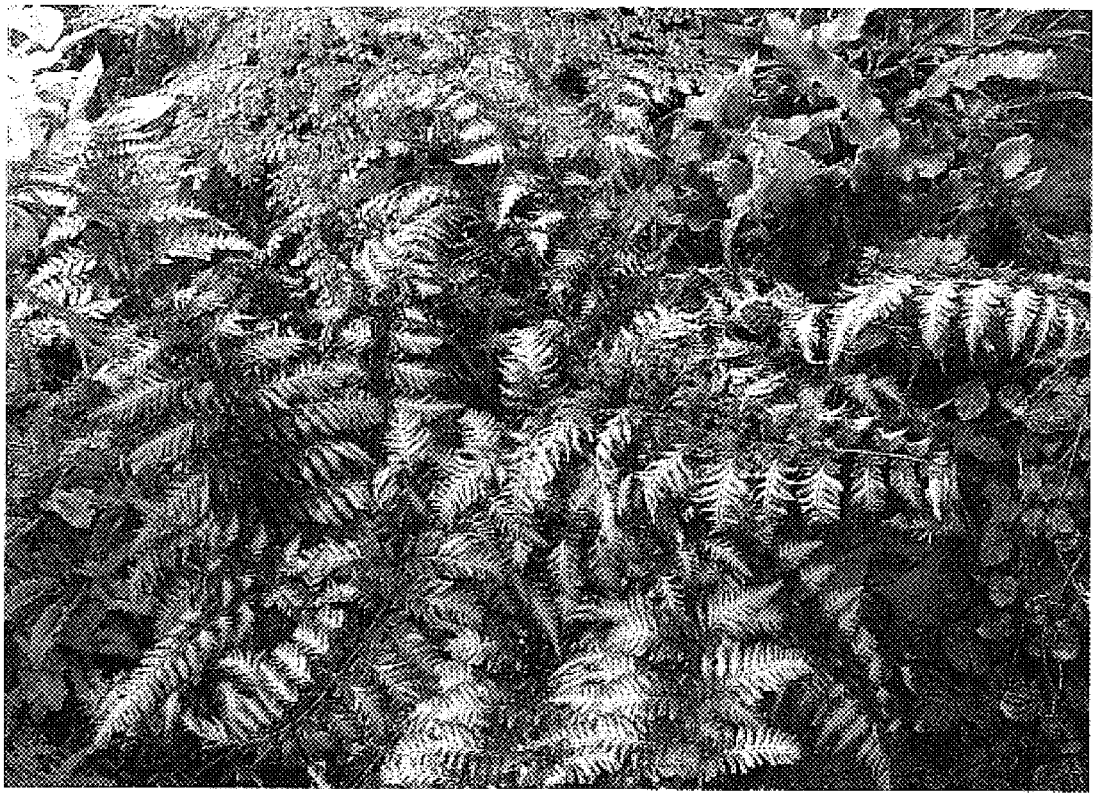

* * * * *